United States Patent
Ramos et al.

Patent Number: 6,016,191
Date of Patent: Jan. 18, 2000

[54] APPARATUS AND TOOL USING TRACERS AND SINGLES POINT OPTICAL PROBES FOR MEASURING CHARACTERISTICS OF FLUID FLOW IN A HYDROCARBON WELL AND METHODS OF PROCESSING RESULTING SIGNALS

[75] Inventors: Rogerio Tadeu Ramos, Brookfield, Conn.; Kenneth Stephenson, Cambridge, United Kingdom

[73] Assignee: Schlumberger Technology Corporation

[21] Appl. No.: 09/074,345

[22] Filed: May 7, 1998

[51] Int. Cl.$^7$ ................................. G01N 33/28
[52] U.S. Cl. .............................................. 356/70
[58] Field of Search ........................ 356/70, 73, 300, 356/326, 337, 338, 342, 343, 402, 432

[56] References Cited

U.S. PATENT DOCUMENTS

| | | | |
|---|---|---|---|
| 4,974,446 | 12/1990 | Vigneaux | 73/155 |
| 5,130,534 | 7/1992 | Gouirand | 250/227.3 |
| 5,166,747 | 11/1992 | Schroeder et al. | 356/326 |

FOREIGN PATENT DOCUMENTS

| | | |
|---|---|---|
| 0 394 085 A1 | 10/1990 | European Pat. Off. . |
| 2 616 909 | 6/1987 | France . |

OTHER PUBLICATIONS

"Void Fraction measurement by a computerized double-point resistivity probe", by Behnia and Gillespie, Flow Meas. Instrum., vol. 2, Oct. 1991.

"Multiple optical fiber probe techniques for measuring profiles of gas–liquid interface and its velocity", by Sekoguchi et al., ASME, Nov. 1985, pp. 97–102.

FloView, stat sheet, for Schlumberger, Nov. 1996.

*Primary Examiner*—Frank G. Font
*Assistant Examiner*—Michael P. Stafia
*Attorney, Agent, or Firm*—David P. Gordon; William B. Batzer

[57] ABSTRACT

Single point optical probes for measuring three-phase characteristics of fluid flow in a hydrocarbon well and methods of processing signals generated by the probe are disclosed. A single fiber optic probe is coupled to a light source and apparatus for detecting reflectance and fluorescence. Light is delivered to the tip of the probe where it either exits the probe and illuminates the liquid ambient the probe tip or is internally reflected in the probe when gas is present at the probe tip. If the fluid at the probe tip is oil, the light exits the probe, illuminates the oil, and causes the oil to fluoresce. Signal processing methods for determining holdup are disclosed. According the invention, a method for determining continuous phase velocities includes injecting a fluorescent dye into the fluid at a measured distance upstream of a probe. The time between injection and detection of the dye is used to calculate average continuous phase velocity. A water soluble dye is used to detect the velocity of water, and an oil soluble dye is used to detect the velocity of oil.

20 Claims, 11 Drawing Sheets

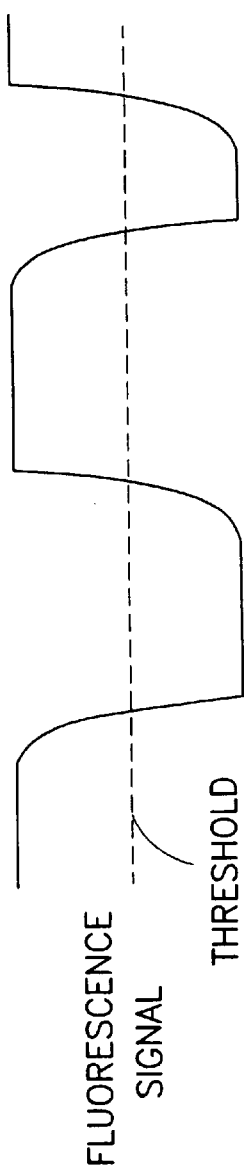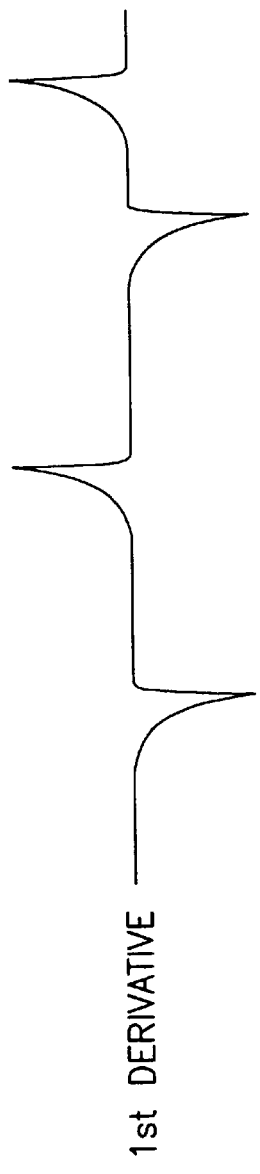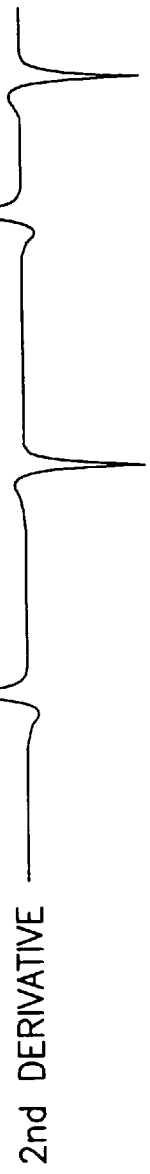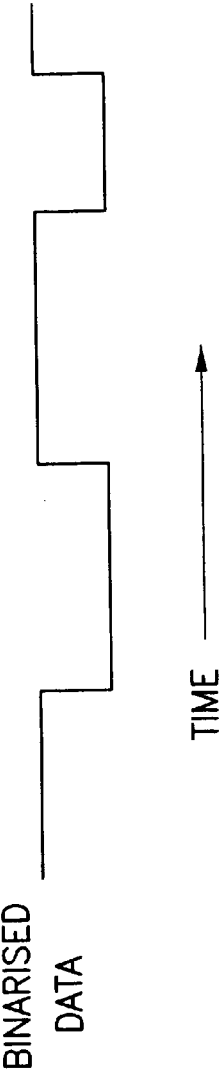
FIG.5a FLUORESCENCE SIGNAL / THRESHOLD
FIG.5b 1st DERIVATIVE
FIG.5c 2nd DERIVATIVE
FIG.5d BINARISED DATA
TIME →

APPARATUS AND TOOL USING TRACERS AND SINGLES POINT OPTICAL PROBES FOR MEASURING CHARACTERISTICS OF FLUID FLOW IN A HYDROCARBON WELL AND METHODS OF PROCESSING RESULTING SIGNALS

This application is related to co-owned Ser. No. 8/793,166 now U.S. Pat. No. 5,831,743, entitled "Optical Probes", filed Feb. 6, 1997, the complete disclosure of which is hereby incorporated by reference herein.

BACKGROUND OF THE INVENTION

1. Field of the Invention

The invention relates to methods and apparatus used to measure the characteristics of fluid flowing through a well during hydrocarbon production. More particularly, the invention relates to a probe and signal processing methods for determining the volumetric flow rates of one or more of the fluid constituents in a well, and preferably for also determining the proportional volume of oil, gas, and water constituents in a well.

2. State of the Art

After drilling is completed, in many hydrocarbon wells the borehole is lined with a casing. In order to extract hydrocarbon fluids (oil and gas) from the formation surrounding the borehole, holes are made in the wall of the casing. The location of the holes is usually determined by reference to information acquired about the formation during the drilling operation, and/or after drilling with the aid of logging instruments before the casing is installed.

Various methods are used to urge the fluid out of the formation, into the well, and up to the surface. In most cases, the fluid travelling to the surface is a mixture of two or three fluid components (phases): oil (liquid hydrocarbon), hydrocarbon gas, and water (or brine). The fluid is collected at the surface and is handled in different ways, depending on the relative proportion of each phase. For example, if the fluid contains a relatively small amount of gas, the gas may be burned at the well site since it is not economically practical to process small amounts of gas. If the fluid contains relatively large amounts of water, it may be economically impractical to continue production operations at the site. In fact, even while the well is producing petroleum products, the disposal of water produced from the well is very costly. In general, the different phases of the well fluid enter the well from different locations, and a high water content can be the result of improperly located perforations in the casing. If it is possible to determine where water is entering the well, perforations in the casing can be plugged and the proportional amount of water in the fluid reduced.

The relative volumetric flow rates (flow rate fractions) of the oil, gas, and water through the well is known in the art as the "cut". The "holdup" is a measure of relative proportions of each phase in a selected volume of fluid in the well; i.e., the volume fraction. The cut and holdup are not in general the same, because the different phases may be, and are in general, flowing at different average speeds. In addition, both the volumetric flow rate and the volume fraction will vary over time and vary at different depths in the well.

Various methods and devices have been used for many years to estimate the volumetric flow rate and the holdup of each phase at different depths in a well over time. Most of the methods of the prior art measure volumetric flow rate or holdup averaged over the cross-sectional area of the wellbore. The principal devices for measuring flow rates employ propellers or turbines which are assumed to measure the average volumetric flow rate of the entire fluid mixture. However, propellers and turbines are typically ineffective in providing even their limited quantitative measurement when the well is not substantially vertical (i.e., when the well deviates more than five degrees from vertical). Other devices of the art measure differential pressure to determine the average density of the flowing mixture. These devices lose their accuracy when fluid flow rate is high or the well is substantially inclined. Still other methods and devices for measuring holdup include the use of electrical plates to measure capacitance of the fluid and make a determination of the fluid content based on variations in capacitance. Similar systems measure resistivity or measure dielectric constant in the presence of RF radiation.

Recent devices derive the wellbore cross-sectional averaged volumetric flow rate and holdup from a number of local measurements made within the wellbore. The accuracy of these averaged volumetric flow rate and holdup determinations depends on the accuracy of each local sensor (probe), the deployment of a sufficient number of probes, and, in the case of non-vertical wells, knowledge of multiphase flow in the inclined pipe. Thus far, the local sensors which have been used have been electrical sensors which respond to the resistivity of the fluids in the wellbore. However, electrical probes can only measure the holdup and volumetric flow rates of the dispersed phase (which in an oil-water system at an oil holdup of more than about 0.65 is the water).

A known method for measuring liquid flow rates of a continuous phase consists of injecting a radioactive tracer at a location downhole and detecting its later arrival at a location relatively uphole. However, the use of radioactive tracers is generally considered undesirable. Recently, non-radioactive gadolinium has been used as a tracer and detected by a pulsed neutron tool. However, the use of the pulsed neutron tool is known to have many disadvantages.

In order to overcome many of the disadvantages of the prior art, the previously incorporated related patent application suggests utilizing pairs of adjacent optical fiber probes as part of a tool which distinguishes between the phases of a multiphase fluid flow in a borehole. According to the related patent application, optical reflection measurements can discriminate between gas and liquid because of the relatively large contrast in the signal received when gas is present and when liquid is present. However, it is much more difficult to distinguish between oil and water because of the lower and variable contrast existing between the oil and water signals. State-of-the-art three-phase optical probes utilize the principle of total internal reflection (which relates to the refractive index of a fiber optic probe and the refractive index of fluid at the tip of the probe) to make a determination of whether the fluid is a gas or a liquid. These systems, which are disclosed in the previously incorporated related application, utilize oblique ended probes where the angle of the tip face is carefully chosen relative to the refractive indices of the fluid components. In addition, the probe tip is preferably coated in order to prevent water wetting of the probe tip from interfering with oil detection.

While it is theoretically possible to construct a single reflection probe which can distinguish oil from water and liquid from gas, it is at best difficult to do so using the techniques of the prior art. Due to the complications in choosing the correct angle, correctly orienting the probe, and coping with temperature and/or salinity induced changes in the refractive index of water, using prior art techniques, it is difficult to provide a single reflection probe with the ability to properly distinguish each of the three phases of fluid. Therefore, more robust reflective optical fluid analysis systems such as that disclosed in the related patent application utilize a pair of probes which are located in close proximity to each other. One probe is designed to distinguish liquid from gas and the other is designed to distinguish oil from "not oil". However, it will be appreciated that such systems are still subject to error, as the closely located probes may see different parts of the multiphase fluid stream and may affect the flow around the other and hence the accuracy of measurement.

SUMMARY OF THE INVENTION

It is therefore an object of the invention to provide an optical probe for accurately measuring three-phase holdup in an oil well.

It is also an object of the invention to provide an optical probe for accurately measuring volumetric flow rates of one or more phases in an oil well.

It is another object of the invention to provide a single optical probe which is capable of distinguishing liquid from gas, and oil from non-oil.

It is a further object of the invention to provide optical probes which are capable of measuring both holdup and volumetric flow rates of a production well.

Another object of the invention is to provide methods for processing signals from optical probes to determine the holdup and phase velocity during well production.

In accord with these objects which will be discussed in detail below, the optical probe of the present invention includes a single fiber optic probe which is optically coupled to a light source and apparatus for detecting reflectance and fluorescence. Light is delivered to the tip of the probe where it either exits the probe and illuminates the fluid ambient the probe tip or is internally reflected in the probe by the interface of the probe and fluid at the probe tip. In particular, if the fluid at the probe tip is oil, the light exits the probe, illuminates the oil, and causes the oil to fluoresce. If the fluid at the probe tip is gas, the light is reflected back due to internal reflection (or, if the probe is oil wet, due to the gas-oil interface). If the fluid at the probe tip is water, little or no light is reflected back and the water does not fluoresce. A detection system preferably including at least one beam splitter and fluorescence and reflectance detectors is provided in conjunction with the probe. According to a presently preferred embodiment, the light source and reflectance detector are coupled to the fiber optic by a directional coupler (fiber beam splitter). According to a presently preferred embodiment, the fluorescence detector is coupled to the fiber optic by a wavelength division multiplexer; while according to another embodiment, the fluorescence detector is coupled to the fiber optic by a second directional coupler and an optical filter to block out reflected light and allow fluorescent light to pass. The invention takes advantage of the facts that oil will fluoresce in all directions when exposed to light radiation of a particular wavelength and that the wavelength of the fluorescent light is distinguishable from the wavelength of the incident light radiation which is reflected. The invention makes it possible to discriminate gas, oil, and water at a single point in well fluid thereby providing a more accurate measurement of the three phase holdup.

According to the methods of the invention, light returning from the probe is directed to two detectors, one for fluorescence and one for reflectance. As mentioned above, the preferred method of directing the light to the detectors is by way of a wavelength division multiplexer which passes light of a first wavelength (i.e. the wavelength of the source) to the reflectance detector and light of a second wavelength (i.e. the wavelength(s) of fluorescence) to the fluorescence detector. It has been discovered that by choosing the proper wavelength for the incident light source and properly designing the probe, a signal processing system which requires virtually no calibration can be implemented. According to one embodiment, where the source and detectors are located downhole, the wavelength of the incident light source is preferably approximately 680–690 nm. According to another embodiment, with the source and detectors located downhole, the wavelength of the incident light source is preferably approximately 470 nm. With these wavelengths, fluorescent light and reflected light are easily distinguished, reflected light is detected only in the presence of gas, and fluorescent light is detected only in the presence of oil.

A preferred signal processing system for detecting oil, gas, and water provides two quasi-binary indicators: gas/liquid and oil/not oil. Three of the four possible indications (gas-not oil, liquid-not oil, and liquid-oil) give reliable results indicating whether the fluid at the probe tip is gas, water, or oil. One of the four possible indications (gas-oil), which normally will not occur when proper threshold values are utilized, can be considered an error indicator indicating any of several conditions, e.g. the presence of a thick oil film on the probe tip, a malfunctioning light detector, a malfunctioning light source, malfunctioning optical filters, or two phases on the probe tip.

It has been discovered that the reflectance signal indicating the presence of gas exhibits a rapid change and that a signal threshold indicating the presence of gas is easily established. According to one signal processing method of the invention, the reflectance signal binarized at the threshold to provide a gas/liquid quasi-binary signal which changes over time. A histogram of the signal values is used to calculate the gas holdup.

It has also been discovered that the fluorescence signal does not change as rapidly as the reflectance signal. In particular, the detection of fluorescence begins before the oil drop touches the probe and the intensity of fluorescence decreases before the drop leaves the probe. According to other signal processing methods of the invention, the fluorescence indication signal is processed by taking its derivative (and preferably second derivative) to determine the "corners" of the fluorescence signal over time. The derivative signal exhibits a positive and a negative peak which are separated by time. The first peak indicates the time when the leading edge of an oil droplet or slug arrives at the probe tip. The second peak indicates the time when the trailing edge of the oil passes the probe tip. The amplitude of one of the peaks (the first peak if the signal is the first derivative) provides an indication of the velocity of the oil drop. The time interval (distance) between the peaks provides an indication of the oil holdup.

According to another method of the invention, a fluorescent dye is injected into the continuous phase of a multiphase fluid at a measured distance upstream of a probe, and the time between injection and detection of the dye is used to calculate the velocity of the continuous phase. A water soluble dye is used where the continuous phase is water in order to detect the velocity of the water, while an oil soluble dye may be used to detect the oil velocity when the oil is the continuous phase.

According to a presently preferred embodiment, an existing logging tool is modified to include one or more probes, each with its own light source and detection apparatus located in the logging tool. Alternatively, the probes may be coupled by fiber optic cable to light sources and detection apparatus at the surface.

Additional objects and advantages of the invention will become apparent to those skilled in the art upon reference to the detailed description taken in conjunction with the provided figures.

BRIEF DESCRIPTION OF THE DRAWINGS

FIG. 5a is a schematic illustration of the signal from the fluorescence sensor after filtering;

FIG. 5b is a schematic illustration of the first derivative of the signal of FIG. 5a;

FIG. 5c is a schematic illustration of the second derivative of the signal of FIG. 5a;

FIG. 5d is a schematic illustration of a binarized data signal derived from the signals shown in FIGS. 5a–5c;

DETAILED DESCRIPTION OF THE PREFERRED EMBODIMENTS

Figure 1:
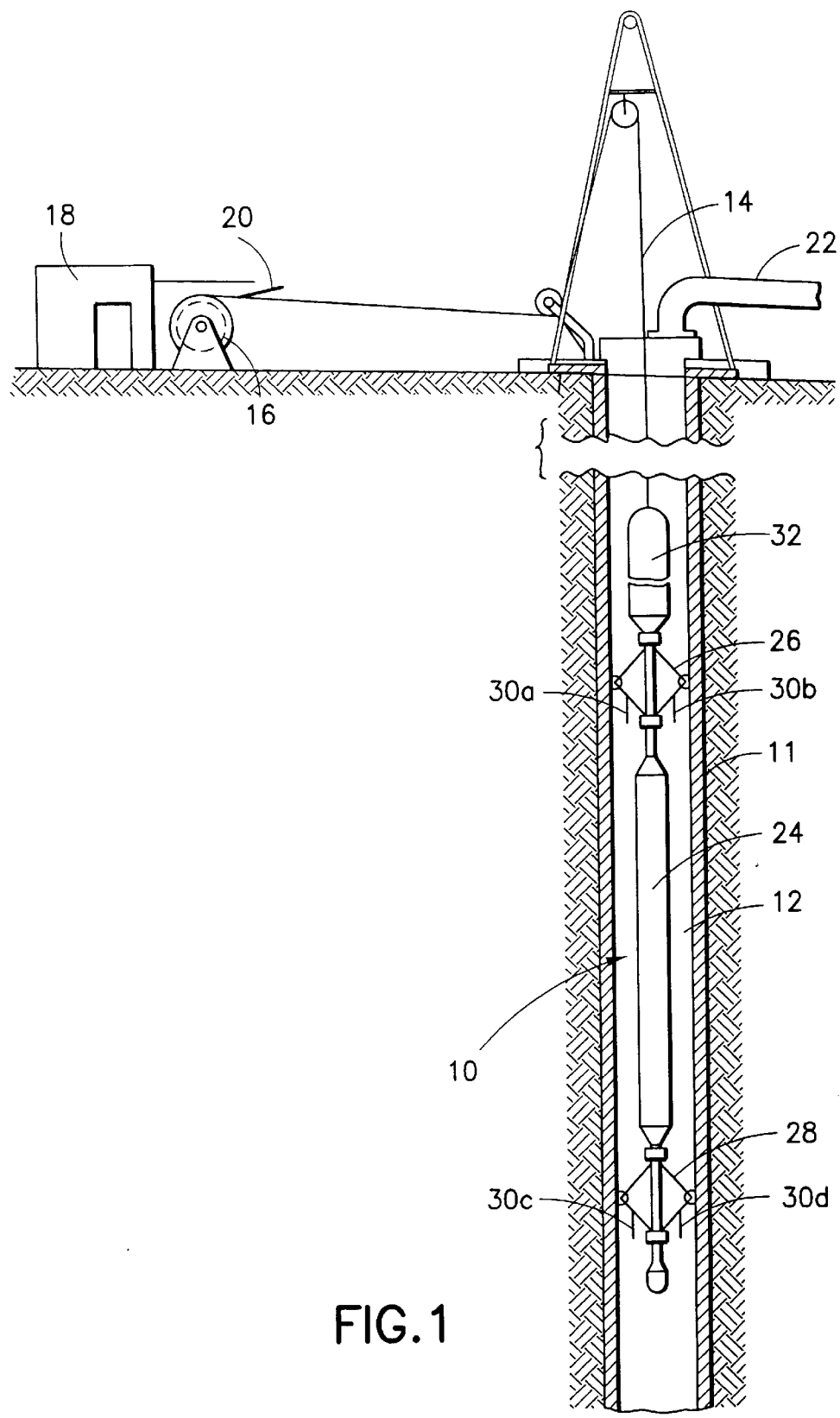
FIG. 1 is a schematic diagram of a production logging tool according to the invention in an oil well and coupled to associated surface equipment.

Referring now to FIG. 1, a production logging tool 10 is suspended in a well 12 by means of a cable 14 which is coupled to a winch 16 for raising and lowering the tool 10. The cable 14 includes conductors (not shown) which may be either electrical or optical, or both, for communicating with data processing equipment 18 located on the surface. A cable displacement detector 20 is also provided at the surface in order to determine the depth of the tool 10 when it is lowered into the well 12. During production, fluid from the well is collected at the surface and conducted by a duct 22 to a storage or refining facility (not shown).

The tool 10, according to the preferred embodiment of the invention, generally includes an elongate body 24 which is preferably centered (or otherwise oriented) in the casing 11 of the well 12 by upper and lower bow springs 26, 28 (although only one set of bow springs is required for centering). The preferred tool 10 of the invention is provided with a plurality of optical probes, e.g. 30a, 30b, 30c, 30d, which are located in the casing by the springs 26, 28. According to one embodiment of the invention, optical source and detection equipment are located in the tool 10, e.g. in an upper electronics housing 32. According to another embodiment, optical source and detection equipment are located with the data processing equipment 18 at the surface.

Figure 2:
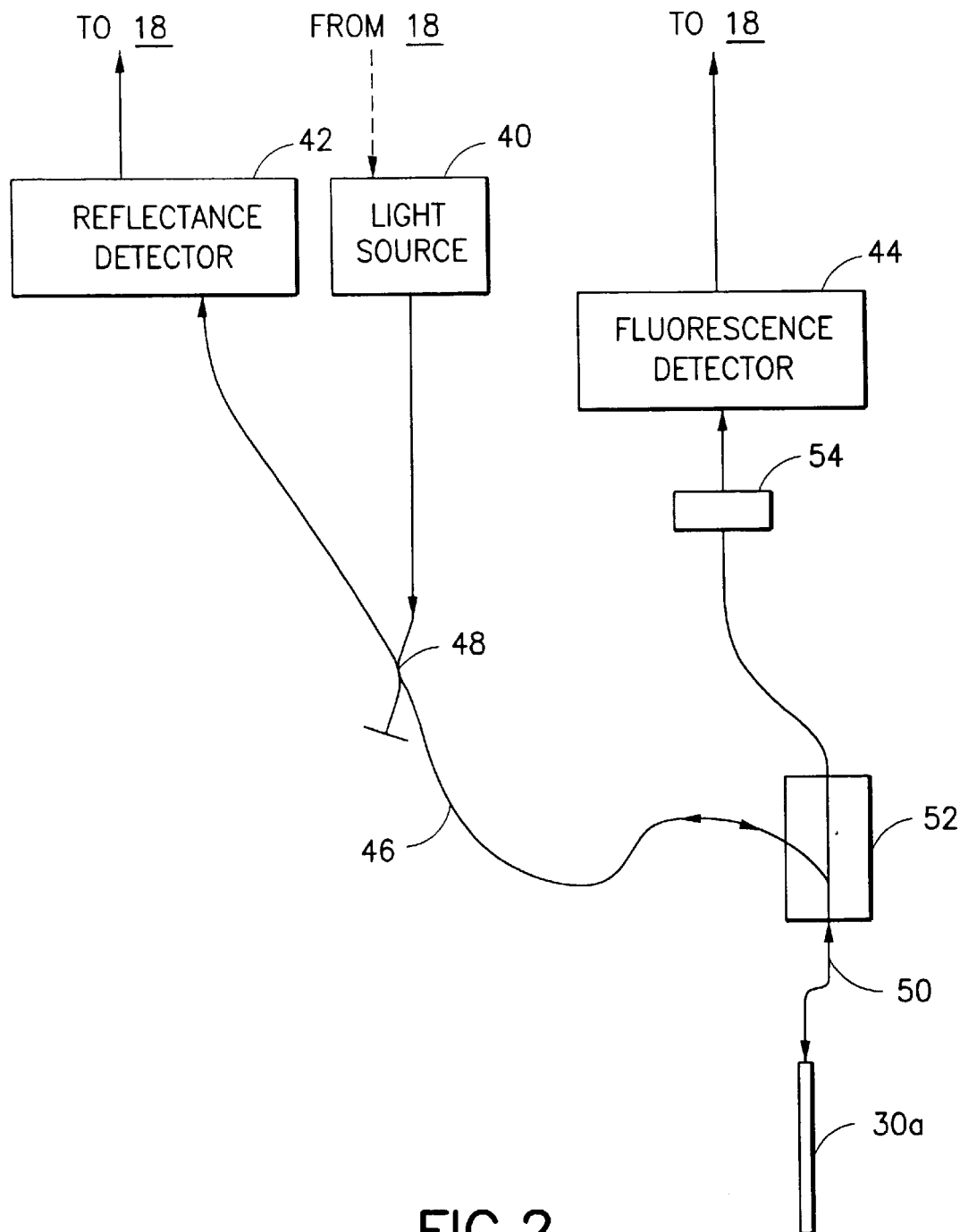
FIG. 2 is a simplified schematic diagram of a presently preferred embodiment of the coupling of a light source and detectors to an optical probe according to the invention.

Turning now to FIG. 2, each optical probe, e.g. 30a, is optically coupled to a respective light source 40, reflectance detector 42, and fluorescence detector 44. According to a presently preferred embodiment, the light source 40 and reflectance detector 42 are optically coupled to a first fiber optic 46 by way of a 1:1 directional coupler (fiber beam splitter) 48. The fluorescence detector 44 and the fiber optic 46 are optically coupled to a second fiber optic 50 by way of a wavelength division multiplexer 52. The second fiber optic 50 is optically coupled to the probe 30a. An optical filter 54 is optionally placed in the optical path between the multiplexer 52 and the fluorescence detector 44. The arrangement source and detectors in this embodiment is designed to operate downhole in the logging tool. Accordingly, according to one embodiment of the invention the light source is a laser diode such as a Honeywell HFE4050 which operates correctly at temperatures up to 100° C. (although other laser diodes or non-laser light sources such as high brightness LEDs can be utilized). The laser diode emits red light in the 680–690 nm range. At this wavelength, oil will fluoresce at a wavelength in the range of 700–850 nm or longer. A suitable multiplexer for isolating fluorescent light in this spectrum is the Muxoptic MX.125 series from ATI Électronique. The use of a multiplexer and the arrangement of the components is aimed at minimizing attenuation of the fluorescent light entering the tip of the probe 30a. This is important because the intensity of the fluorescent light is much lower than the intensity of the light source and the reflected light and, to start with, the intensity of the laser diode and other likely light sources is not very high. The typical attenuation associated with a coupler 48 is approximately 3 dB, but the loss associated with the multiplexer 52 is only 1.5 dB. It will also be appreciated that in order to further minimize attenuation of the fluorescent light, the multiplexer 52 is located in the optical path between the probe 30a and the coupler 48. The optional filter 54 in this embodiment is only necessary if the multiplexer does not sufficiently prevent the detector 44 from seeing reflected light. As described in more detail below with reference to FIGS. 4 and 5, the outputs of the detectors 42, 44 are provided in preprocessed form to data processing equipment 18 (FIG. 1) which is preferably located on the formation surface.

Figure 2A:
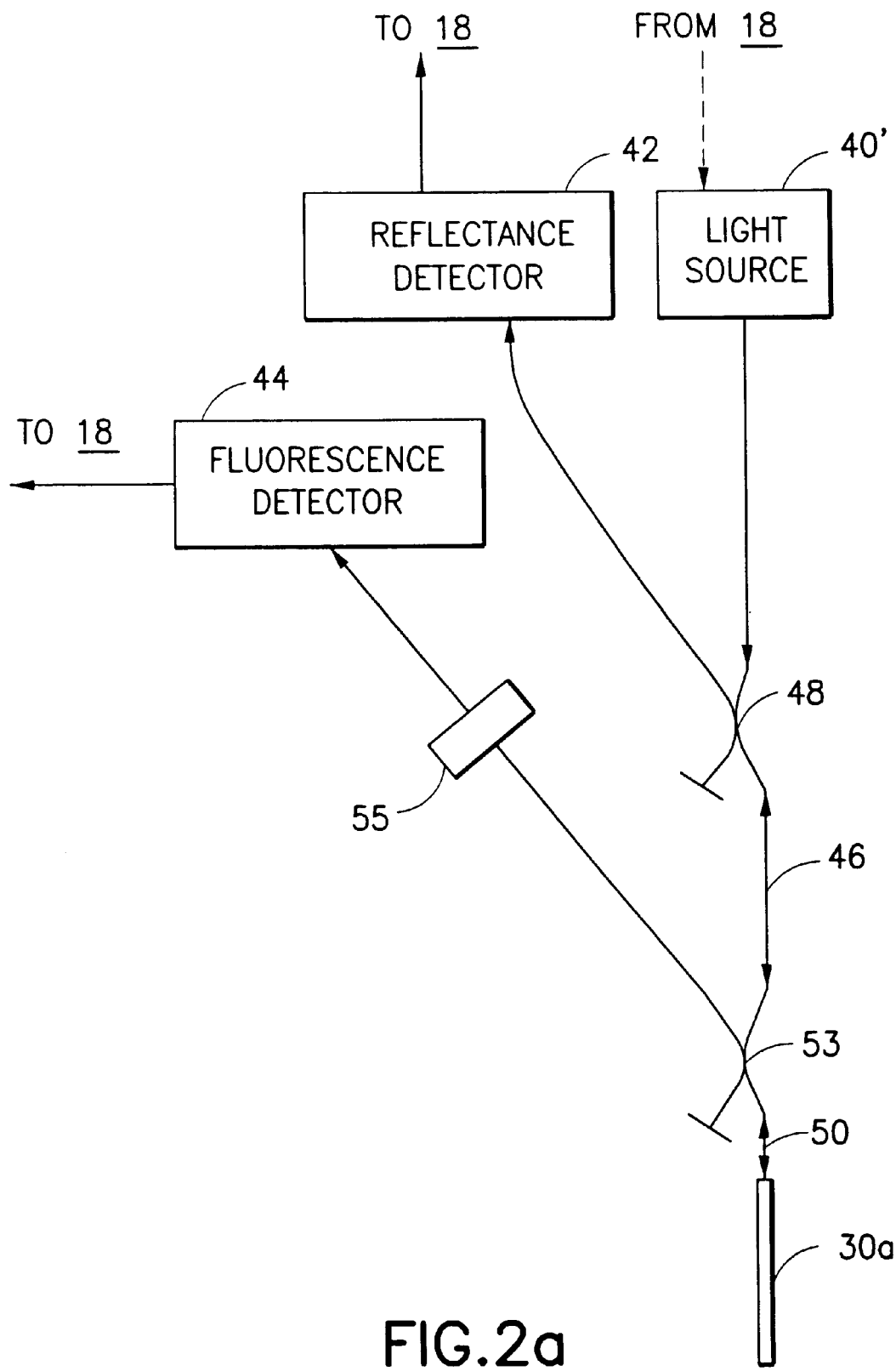
FIG. 2a is a simplified schematic diagram of an alternate embodiment of the coupling of a light source and detectors to an optical probe according to the invention.

An alternative arrangement of probe, source and detectors is shown in FIG. 2a. In this arrangement, there is significantly more attenuation, but the need for a multiplexer is eliminated. Thus, according to this embodiment, light source 40' and reflectance detector 42 are coupled to the first optic 46 by way of the 1:1 directional coupler (fiber beam splitter) 48. The fluorescence detector 44 and the fiber optic 46 are optically coupled to the second fiber optic 50 by way of another fiber beam splitter 53 and the second fiber optic 50 is optically coupled to the probe 30a. An optical filter 55 is placed in the optical path between the splitter 53 and the fluorescence detector 44 to prevent the detector 44 from detecting reflected light. A possible alternative to the use of the filter 55 is to provide a fiber optic with an internal grating which acts as a filter. As described in more detail below with reference to FIGS. 4 and 5, the outputs of the detectors 42, 44 are provided in preprocessed form to data processing equipment 18 (FIG. 1) which is preferably located on the surface. In addition, according to one embodiment of the invention discussed below, the light source 40' is also controlled according to a duty cycle by the data processing equipment 18 or by downhole electronics (not shown) in housing 32 or body 24.

As mentioned above, the light source and the detectors may be located downhole in the tool or uphole with the data processing equipment. When located downhole, a compact laser diode is an appropriate light source, although other light sources high brightness LEDs may be utilized. When located uphole, however, a more powerful light source such as a higher powered laser is appropriate. Those skilled in the art will appreciate that the detectors may be fabricated from any photodetector suitable for use with the particular light source given the wavelength and intensity of the source. For example, if the light source is the laser diode mentioned above, a suitable detector would be a Honeywell HFD3022. Alternatively, if an LED with optical output of 470 nm is used, a suitable detector would be a high temperature photomultiplier such as the EMR 741N available from EMR of Princeton, N.J.

Figure 3D:
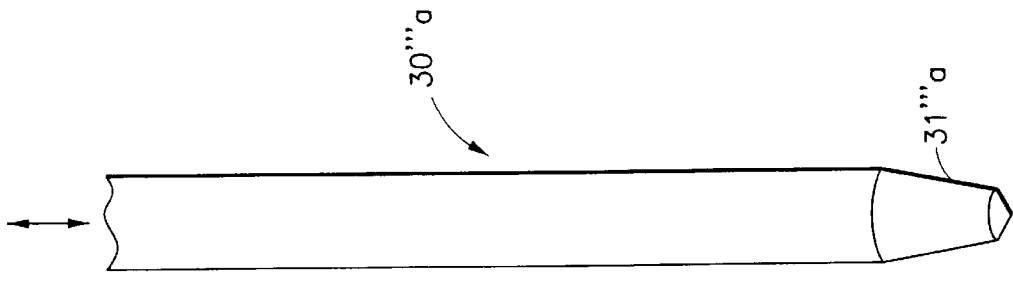
FIG. 3d is a schematic diagram of a biconical sapphire optical fiber probe.
Figure 3C:
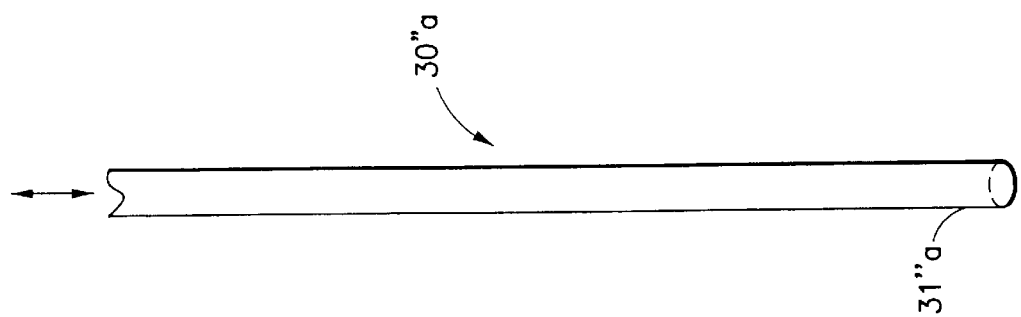
FIG. 3c is a schematic diagram of a flat or cleaved silica optical fiber probe.
Figure 3B:
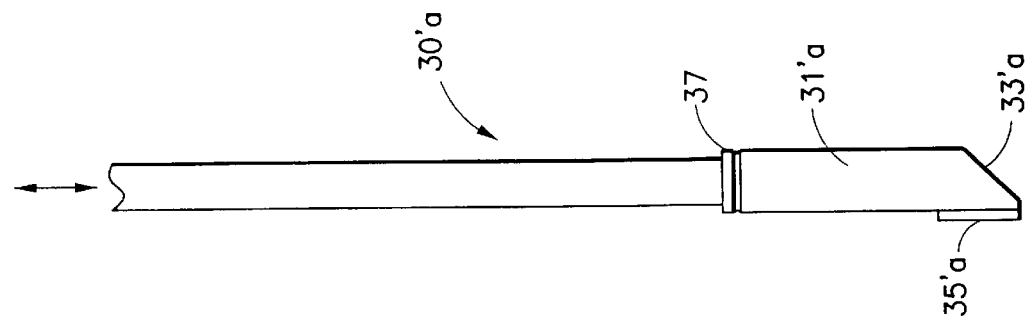
FIG. 3b is a schematic diagram of a silica optical fiber probe with a sapphire fiber probe tip.
Figure 3A:
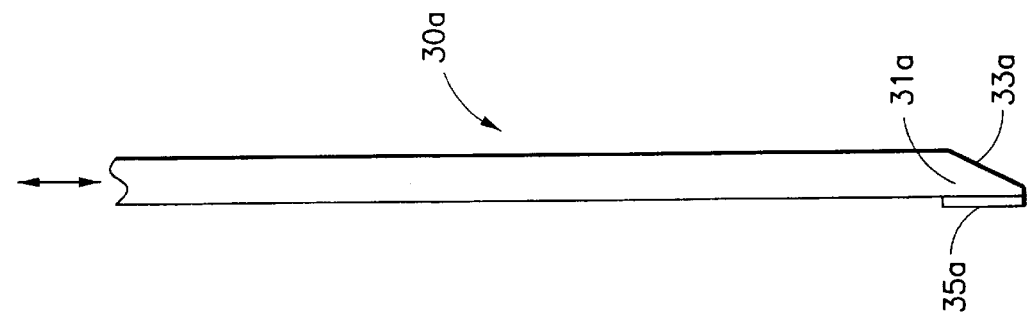
FIG. 3a is a schematic diagram of oblique tip silica optical fiber probe.

Turning now to FIGS. 3a–3d, four examples of different fiber optic probes which may be used as probes of the invention are seen. The fiber optic probe of FIG. 3a is provided with an oblique tip as described in the previously incorporated related patent application. The use of an oblique tip is believed to provide a gas detection signal of greater intensity. Thus, according to the embodiment of FIG. 3a, a probe 30a is made of a standard fused silica optical fiber (with a high temperature cladding). The tip 31a of the probe 30a is provided with a 60° sensor surface 33a. This angle is based on the refractive indices of gas, borehole liquids (e.g., water, brine, oil), and fused silica. A reflective corner coating 35a is preferably provided behind the sensor surface 33a. The reflective coating may be applied by metal vapor deposition onto the cladding of the fiber optic probe. In order to avoid the adverse effects of film buildup on the probe tip, it is preferable to use a fiber optic with a relatively small diameter. However, if the diameter is too small, light throughput may be a problem. A presently preferred diameter is approximately 100–300 microns. However, fiber optics having a diameter between approximately 10 microns and 1,000 microns will work well.

Those skilled in the art will appreciate that it is important that the probe (or the portion of the probe which is exposed to well fluids) be resistant to abrasion. An alternative design for the probe is shown in FIG. 3b. The probe 30'a is provided with a sapphire fiber tip 31'a which is coupled to a standard fused silica optical fiber (with a high temperature cladding) via an optional quarter wavelength impedance transformer 37. The sapphire tip is preferably provided with a 45° sensor surface 33'a and a reflective coating 35'a behind the sensor surface. The 45° angle is based on the refractive indices of gas, borehole fluids, and sapphire. In addition to being resistant to abrasion, the sapphire probe with an optical incidence of 45° provides a very accurate discrimination between gas and liquid in downhole conditions in that the discrimination is robust against variations in salinity, temperature and pressure.

Turning to FIG. 3c, a third probe 30"a is seen with a flat or cleaved tip 31"a. The third probe is preferably formed from a standard silica optical fiber. It will be appreciated that while the third probe does not have an oblique tip, it can still be used effectively, because the detection of oil does not require reflection, and because some light will be reflected at the interface between the fiber tip and gas. A fourth probe 30'''a is seen in FIG. 3d. Probe 30'''a includes a biconical sapphire tip 30'''a which is optically attached to a standard silica optical fiber.

Figure 4:
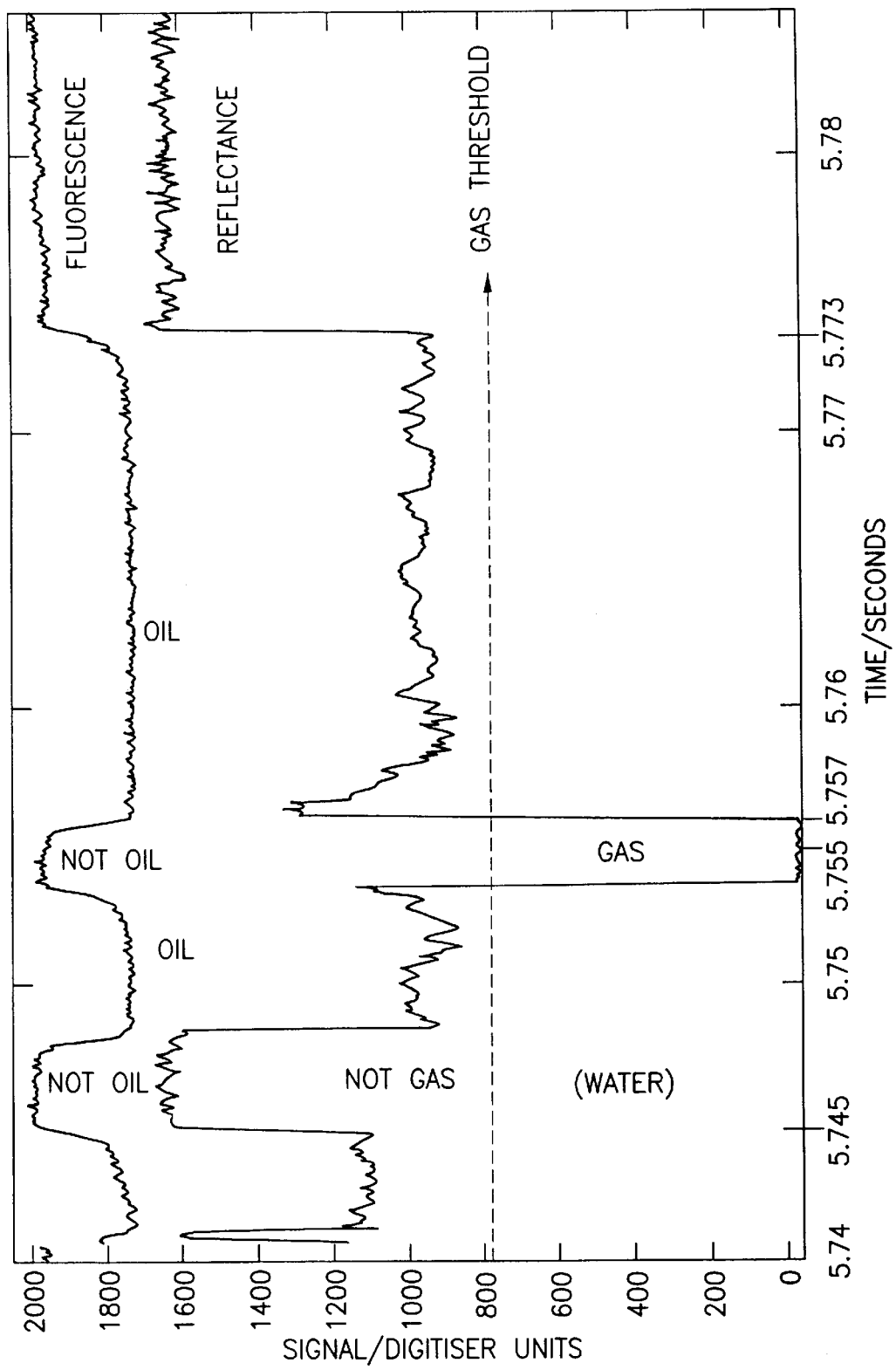
FIG. 4 is an graph showing exemplary signals from the reflectance and fluorescence sensors.

As mentioned above, the detectors coupled to the probe will output signals over time indicating whether the fluid passing across the probe tip is gas or liquid and whether the liquid is oil or not oil. An exemplary plot of the types of signals recorded from the detectors is shown in FIG. 4. The upper plot shows the output of the fluorescence detector and the lower plot shows the output of the reflectance detector. The plots are synchronized and represent detector outputs over a time period indicated on the X-axis in FIG. 4. The outputs of the detectors shown in FIG. 4 were amplified by an inverting amplifier. Therefore, the detections of fluorescence and reflectance are indicated by low signals in FIG. 4. The signal strength indicated by the Y-axis in FIG. 4 is measured in "digitizer units" where 2048 digitizer units equals 5 V. As seen in FIG. 4, the output of the reflectance detector exhibits some activity which follows the output of the fluorescence detector. This is considered noise so long as the signal level remains above a threshold which has been established for detecting gas by reflection. As shown in FIG. 4, this gas threshold level is indicated at zero digitizer units. It will be appreciated that a quasi-binary indication of the presence of gas can be obtained by noting whenever the reflectance signal crosses the gas threshold.

With the gas/liquid and oil/not-oil determinations, three of the four possible indications (gas-not oil, liquid-not oil, and liquid-oil) give reliable results indicating whether the fluid at the probe tip is gas, water, or oil. One of the four possible indications (gas-oil), which normally will not occur when proper threshold values are utilized, can be considered an error indicator indicating any of several conditions, e.g. the presence of a thick oil film on the probe tip, a malfunctioning light detector, a malfunctioning light source, malfunctioning optical filters, or two phases on the probe tip.

According to the invention, rising and falling transition signals seen in FIG. 4 provide a reliable indication of the detection of an oil drop touching the probe. This is because the transition time for the fluorescence signal is characteristically longer than the transition time for the reflectance signal. In particular, the fluorescence signal starts to change before an oil drop touches the probe and before the oil drop leaves the probe. These transitions can be seen best in FIG. 4 at the times t=5.745 through t=5.773. It should be noted that the leading and trailing transitions are different. It has been discovered experimentally (using high speed synchronized photography) that the reflectance signal and the fluorescence signal coincide at the moment an oil drop touches the probe. For example, at t=5.757 in FIG. 4, the leading edge of the fluorescence signal ends at the moment the reflectance signal shows its rapid transition from indicating gas to indicating not gas, i.e. the fluorescence signal grows in amplitude as the oil drop approaches the probe until the moment it touches the probe. As explained in more detail below, the fluorescence signal transition time, e.g. from t=5.755 to t=5.757, of the fluorescence signal can be used to determine the velocity of the oil drop approaching the probe.

In order to determine oil holdup, however, it is necessary to determine the total time when the oil drop is actually touching the probe. As shown in FIG. 4, an example of this time is indicated from t=5.757 through t=5.773, the time from when the leading edge of the signal ends to the time where the trailing edge of the signal ends.

It has been found by the inventors that if the probe is provided with an oblique tip as described above with reference to FIGS. 3a and 3b, it may be difficult to detect the leading edge of oil fluorescence following a transition from gas if the gas causes total internal reflection in the probe. In such a case, gas to oil transitions will show a sharp change in the fluorescence signal and it may be desirable to determine oil velocity during water to oil transitions.

Figure 5:
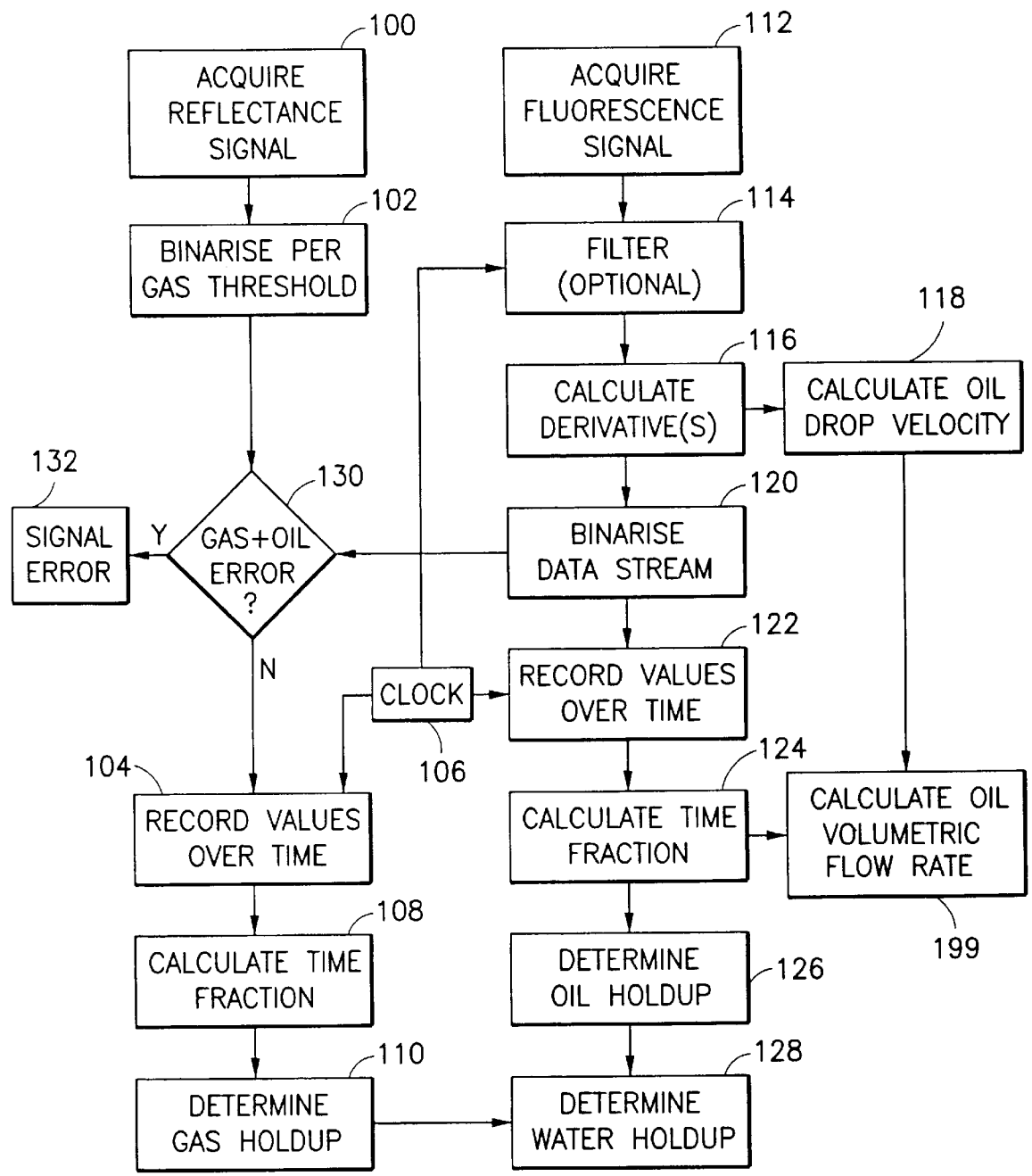
FIG. 5 is a schematic block diagram of a signal processing method according to the invention for determining holdup and oil velocity.

Turning now to FIGS. 5, and 5a–5d, the signals from the fluorescence and reflectance detectors may be processed in a number of ways to provide an indication of holdup and/or an estimation of the volumetric flow rate in a well. As mentioned above, the quantification of the gas component holdup can be made by an historical analysis of quasi-binary values recorded over time. For example, as shown in FIG. 5, the reflectance detector signal is acquired at 100 and is binarized at 102 by comparing the signal level to the gas threshold at 102. These quasi-binary values are recorded over time at 104 with the aid of a clock signal 106. The historical record of the signal indicates at what times gas was detected over a given period of time. It will be appreciated that this indication is theoretically proportionally congruent to the volumetric proportion of gas in the well fluid during the same given period of time. It is theoretically proportionally congruent because the probes do not detect the contents of an entire cross section of the well. However, as described above, the careful location of several probes at a given depth can provide an accurate assessment of the contents of an entire cross section at that depth. Thus, the historical binarized signal is used to calculate a time fraction (a proportional analysis of the ratio of "time high vs. total measurement time") at 108. The analysis will yield at 110 an accurate estimate of the gas holdup for the given period of time which may conveniently be represented as a simple percentage of the well fluid.

The measurement of the oil holdup according to the invention preferably utilizes more signal processing than the measurement of the gas holdup. As shown in FIG. 5, the fluorescence signal is acquired at 112 and may be filtered at 114 if desired to remove noise. According to one method of the invention, the signals are filtered with a time gate which may use the same clock signal 106 as used to record binarized reflectance signal as described above. The filter at 114 will eliminate noise; i.e., it will eliminate signals with rise or fall times or magnitudes which substantially deviate from the magnitudes or average rise and fall times of the leading and trailing edges of the fluorescence signal oil indication. After filtering, the signal is subjected to differentiation at 116 to obtain first (and preferably second) derivative signals which exhibit peaks at the "corners" of the fluorescence signal indicating the times when an oil drop contacts the probe and leaves the probe. FIG. 5a shows a sample of a filtered fluorescence signal. FIG. 5b shows a first derivative of the signal. FIG. 5c shows a second derivative of the signal which has slightly sharper peaks than the first derivative. According to one aspect of the invention, the speed of the oil drop can be calculated at 118 from the amplitude of the first peak of the first derivative signal. More particularly, it will be appreciated that for a given oil, the fluorescence signal f is solely determined by the position x of the oil drop relative to the probe; i.e., f=F(x). Since $$\frac{dF(x)}{dt} = \frac{dF(x)}{dx} \cdot \frac{dx}{dt},$$

the oil speed v can be calculated according to:

$$v = \frac{dx}{dt} = \frac{\frac{dF(x)}{dt}}{\frac{dF(x)}{dx}} \tag{1}$$

Equation (1) is true for any time t and any location x. In addition, the maximum value of the first derivative $$\frac{dF(x)}{dt}$$

corresponds to x=0 (the point at which the oil touches the probe). It should be appreciated that the first derivative $$\frac{dF(x)}{dt}$$

can be conveniently obtained from a simple RC differentiating circuit.

According to another aspect of the invention, the time location of the peaks of the first or second derivative signals are used to generate a binarized data stream at 120. The binarized data stream is shown, e.g., in FIG. 5d. This data is recorded over time at 122 using the same clock signal from 106 which was used to record the reflectance signal. A time-proportional analysis of the binarized signal is performed at 124 and the oil holdup is determined at 126. For example, the time proportion of the oil holdup $h_0$ can be expressed as the quotient shown in Equation 2 where $\tau_i$ is the signal duration of a single event (oil drop) and N is the number of events in a time interval T:

$$h_0 = \frac{1}{T}\sum_i^N \tau_i \tag{2}$$

Given the oil holdup determined at 126 and the gas holdup determined at 110, the water holdup is calculated at 128 by finding the difference between the sum of the oil and gas holdup and 100%.

One of the advantages of oil velocity and holdup measurements according to the invention is that velocity is measured for the same individual oil drops that are measured to calculate holdup. This eliminates errors caused by the fact that the velocity of oil drops vary with their size and location, and possibly their mutual interaction. The volumetric flow rate of oil passing through an area σ is given as:

$$q_0 = \frac{\sigma}{T}\sum_i^N \tau_i v_i \tag{3}$$

Since the product $\tau_i v_i$ ties the size with velocity of each drop, Equation 3 provides a precise calculation of local volumetric flow rate. Thus, as seen in FIG. 5, the oil drop velocity $v_i$ calculated at 118 and the time fraction for that oil drop calculated at 124 can be used to determine the volumetric flow rate for the oil ($Q_o$) at 199. The total volumetric flow rate is obtained by combining the local flow rates $q_o$ (see equation (3)) determined by several probes in different segments of the cross sectional area of the flow. This is true whether the multiphase flow is occurring in a vertical well, a horizontal well, or through an inclined well.

As mentioned above, the binarized data streams generated at 102 and 120 in FIG. 5 are time synchronized and may, under certain conditions, provide contradictory indications. For example, the gas signal may indicate the presence of gas at the same time the oil signal indicates the presence of oil. This "error condition" may be detected by comparing the data streams at 130 and either ignoring the data for that period of time and/or generating an error signal at 132. Another optional signal processing method may be performed by pulsing the light source according to a duty cycle. The pulsed light source provides another way to discriminate between reflectance and fluorescence and thereby eliminate the possible erroneous "gas+oil" indication. The pulsed light source method relies on the fact that oil will continue to fluoresce after the light source is turned off. By time synchronizing the light source and the detectors, it is possible to determine, when the light source is off, whether the signal detected is truly reflectance or fluorescence. In addition, according to this method, it is possible to time the duration of fluorescence after the light source is turned off. It has been recognized that different types of oil exhibit different fluorescence "lifetimes" after the light source has been turned off. Thus, by timing the fluorescence lifetime, it is possible to determine what type of oil is being detected.

Figure 6:
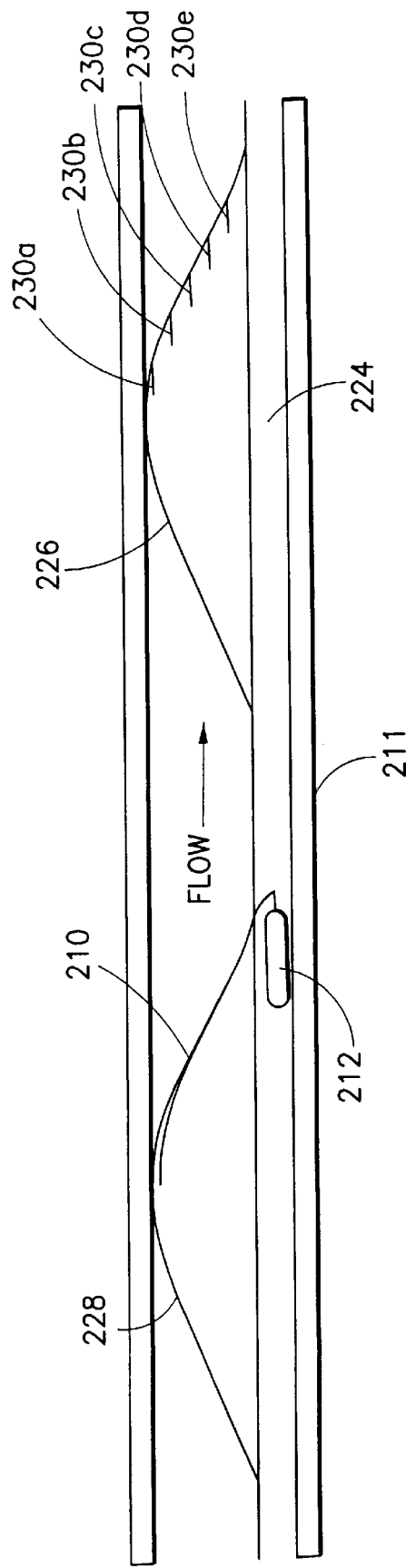
FIG. 6 is a schematic illustration of a logging tool incorporating a tracer injector and detector apparatus according to the invention.

While the oil drop velocity may be determined using the first derivative of the oil fluorescence signal as previously described, according to another aspect of the invention, the oil velocity and/or the water velocity (i.e., the velocity of the continuous phase) may be determined by injecting a fluorescent dye downhole (upstream) of an optical probe and measuring the time between the injection of the dye and the detection of fluorescence at the optical probe. When water is the continuous phase, the water soluble dye (not soluble in gas or oil) is used, while when the oil is the continuous phase, the oil soluble dye (not soluble in water) is used. More particularly, a tracer dye injection and detection system is shown in FIG. 6. The system includes a dye injection tube 210 which is coupled to a source of tracer dyes (not shown) via electrically operated valves (not shown) for injecting a selected amount of the oil or water soluble tracer dye into the flow of fluid inside the casing 211 (which for FIG. 6 is shown to be highly deviated or horizontal). The injection tube 210 is mounted on a first spring bow 228 of an eccentric logging tool 224 and is coupled to an injector 212 which is mounted inside the tool. One or more detection probes (e.g., 230*a*–230*e*) are mounted on a second spring bow 226 which is uphole (downstream) from spring bow 228. Those skilled in the art will appreciate that the probes 230*a*–230*e* may be the same probes which are used to detect the oil, water, and gas holdup and may be coupled to a similar detection system. Thus, the probes would preferably be coupled to a light source and a light detector by an optical fiber, a fiber coupler, and a filter. In one embodiment for detecting the continuous water phase velocity, the filter is a spectral filter which is selected to eliminate substantially all light but for the spectrum of the fluorescent dye. Thus, the tracer being utilized must be chosen to fluoresce in a different spectrum than the spectrum of the oil fluorescence. Alternatively, in another embodiment, the filter may be an intensity threshold filter. In this alternative embodiment, the dye is chosen such that it fluoresces at a high intensity relative to the natural oil fluorescence; thereby distinguishing the dyed water from the oil. Regardless, those skilled in the art will appreciate that if the distance between the injection tube and the probe is known, the velocity of the tracer dye (and thus the fluid it is dissolved in) can be computed by measuring the time between the injection of dye and its detection at the probe.

Figure 7:
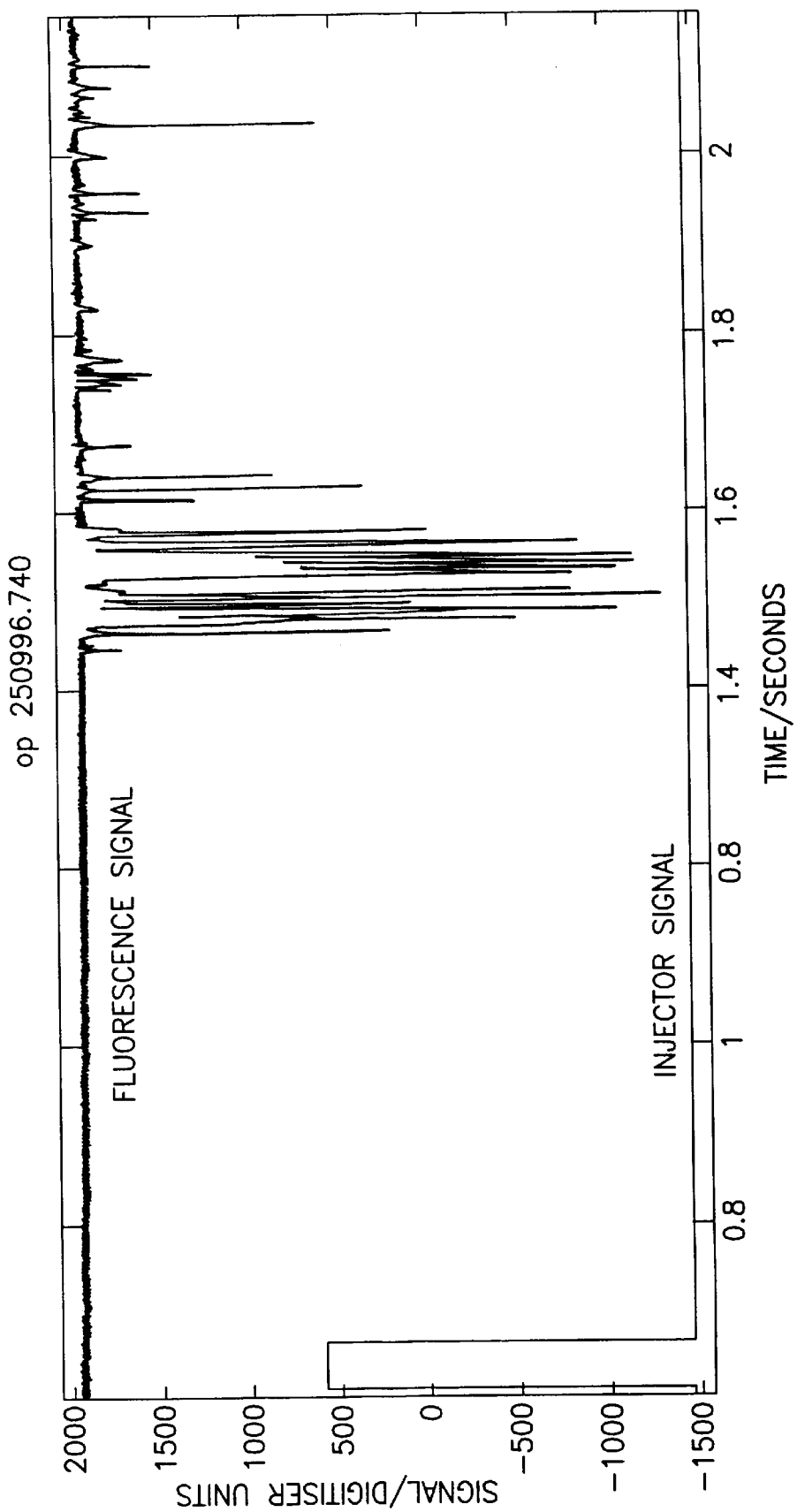
FIG. 7 is a graph of a fluorescence signal from a tracer detector located a distance ten times the well diameter from the injector.

According to the invention, the injection tube and the detection probe should not be located too close together. For example, as shown in FIG. 6, the tube 210 and the probe 230 are spaced apart from each other by a distance "d" in the casing 11 which has a diameter "D". According to the invention, the distance "d" should be carefully chosen relative to the diameter "D" while accounting for the turbulence of the fluid flow in order to ensure mixing of the tracer in the fluid. Often, the Reynolds number for fluid flows downhole is much greater than 2,000. If the probe and the injection tube are too close together, the signal detected when the tracer dye arrives at the probe will exhibit a series of peaks corresponding to pockets of tracer which is not yet well mixed with the fluid. As the probe and the injection tube are located farther apart, the tracer has more time to mix well with the fluid and the signal detected when the tracer dye arrives at the probe should represent a continuous distribution with a single well defined peak indicative of the average velocity of the continuous phase. For example, FIG. 7 shows a plot of the fluorescence signal detected from the tracer dye where the distance between the injector and the probe is d=10D. The square pulse at the left of FIG. 7 indicates the time of tracer injection. The peaks in the fluorescence signal show that the tracer is passing the probe in pockets of different concentration with the first peak indicating the maximum velocity of the tracer in turbulent flow. It is possible for a processor to estimate the average velocity from the maximum using the known well radius and the known radial location of the probe. For example, when the dispersed phase holdup is small, the continuous phase local velocity u at a radial position r can be approximated by Equation 3 where $u_{max}$ is the maximum continuous phase speed and R is the radius of the casing:

$$u \approx u_{\max}\left(\frac{R-r}{R}\right)^{1/7} \quad (4)$$

The average continuous phase speed is given by:

$$\bar{u} = u_{\max}\frac{2\pi}{\pi R^2}\int_0^R \left(\frac{R-r}{R}\right)^{1/7} r\,dr \quad (5)$$

Figure 7A:
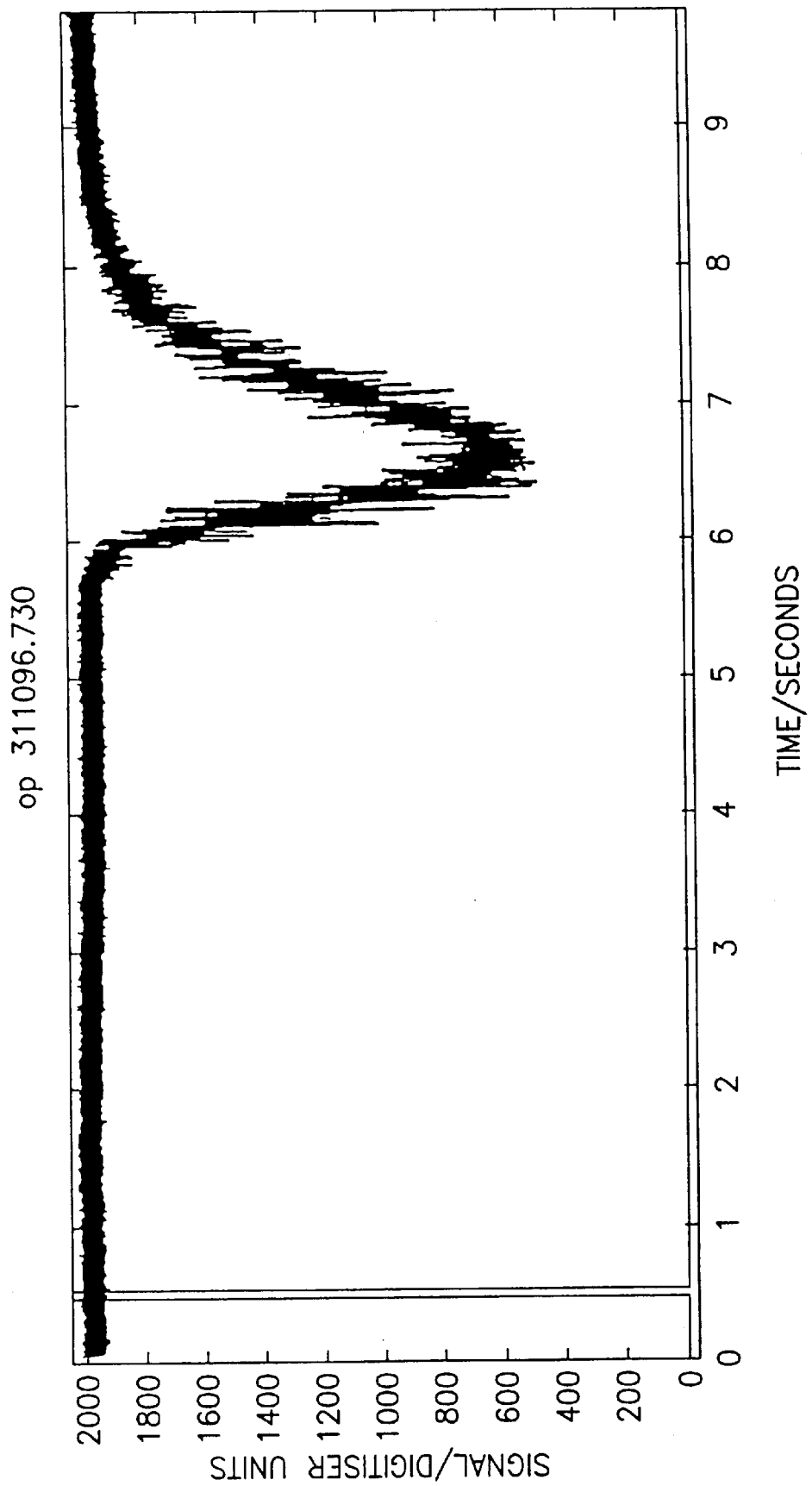
FIG. 7a is a graph of a fluorescence signal from a tracer detector located a distance one hundred times the well diameter from the injector.

It is simpler and more accurate to move the injection tube and the probe farther apart (e.g., preferably d=22; although d may be greater than 22 such as d=40, or d>40). FIG. 7*a* shows a plot of the fluorescence signal detected from the tracer dye where the distance between the injector and the probe is d=100D. The square pulse at the left of FIG. 7*a* indicates the time of tracer injection. The peaks in the fluorescence signal show that the tracer is passing the probe in pockets of different concentration. However, the concentrations are relatively continuously increasing to a recognizable peak concentration (from which an average velocity can be determined) and then relatively continuously decreasing to a level of no concentration of tracer.

Further, if desired, dye uniformity across the fluid flow may be expedited by injecting the dye in a manner perpendicular to the fluid flow. In this manner, the dye will not carry an initial velocity.

While the velocity of the water phase may be determined via dye injection as discussed above when water is the continuous phase of the flow stream, it may also be desirable in some circumstances to measure the velocity and volumetric flow rate of water when it is the discontinuous phase of the flow stream. According to the invention, the velocity of a water drop in a continuous oil phase can be calculated from the amplitude of the certain peaks of the first derivative signal (see FIG. 5b). More particularly, as a water drop approaches the probe, the signal at the fluorescence wavelength decreases in amplitude (signifying the oil-to-water transition). The amplitude of the first derivative of this transition can then be used to determine the discontinuous water phase velocity. Alternatively, the water-to-oil transition can be utilized to determine the water drop velocity. Thus, as the water drop passes the probe, the fluorescence signal increases in magnitude, and the amplitude of the first derivative of this transition can be used to determine the discontinuous water phase velocity.

Figure 8A:
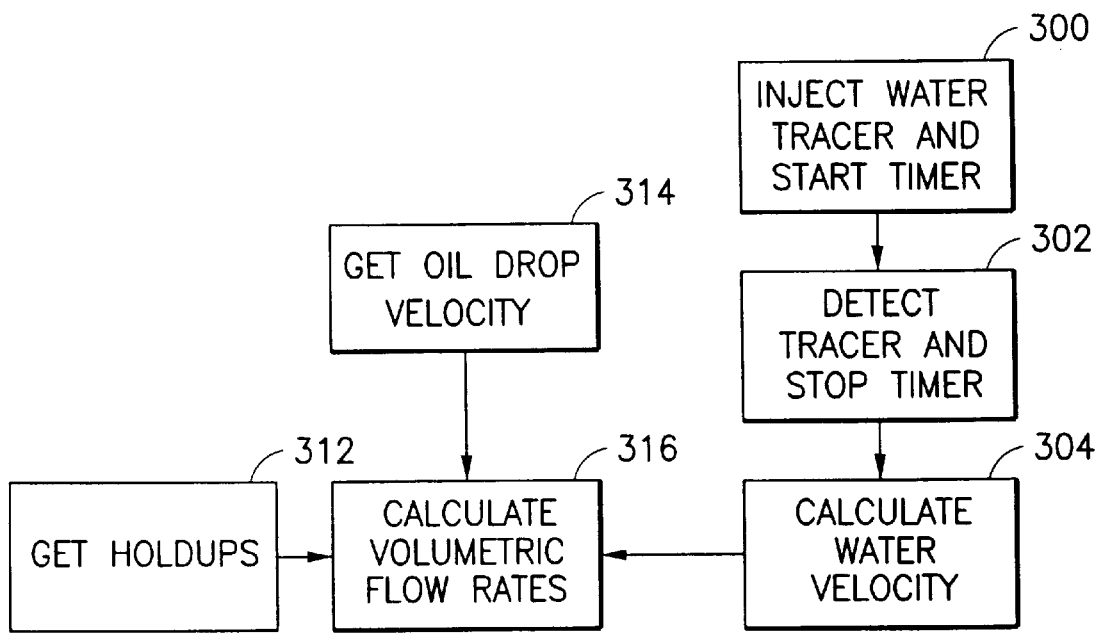
FIGS. 8a and 8b are schematic block diagrams of signal processing methods according to the invention for determining oil and water velocities and volumetric flow rates.
Figure 8B:
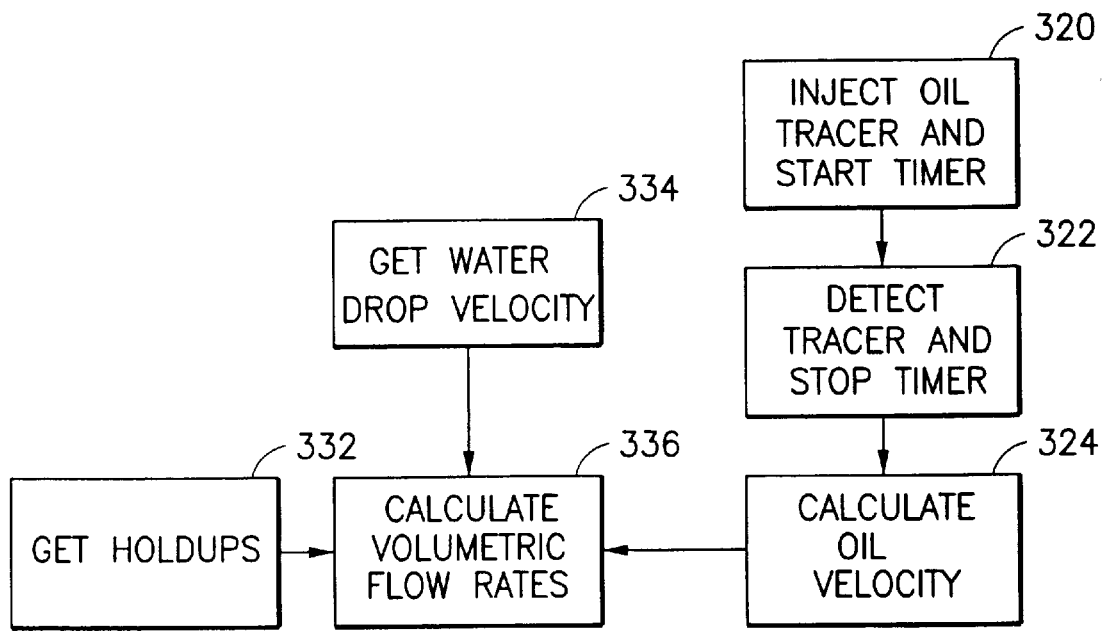

Those skilled in the art will appreciate that once the holdup and average velocities are known, an estimate of the volumetric flow rates can be calculated. FIGS. 8a and 8b show additional exemplary methods according to the invention for calculating the volumetric flow rates after the holdup and the oil and water velocities have been obtained as described above. FIG. 8a includes the steps for calculating water velocity using the system described above with reference to FIG. 6 where water is the continuous phase. In particular, water soluble tracer is injected and a timer is started at 300. The tracer is detected and the timer stopped at 302 when the peak signal is obtained. The time registered by the timer is used to calculate water velocity at 304. Using methods discussed above with reference to FIG. 5, the oil and water holdups are coincidentally determined at 312, and using methods discussed above with reference to FIGS. 5a–5d (i.e., finding the amplitude of the first peak of the first derivative of the fluorescence signal), the oil drop velocity is coincidentally determined at 314. Using the oil and water holdups and the water velocity and oil drop velocity as determined, the water and oil volumetric flow rates are determined at 316.

Similarly, with reference to FIG. 8b where oil is the continuous phase, if desired, an oil soluble tracer may be injected and a timer is started at 320. The tracer is detected and the timer stopped at 322 when the peak signal is obtained. The time registered by the timer is used to calculate oil velocity at 324. Alternatively, the oil velocity may be determined using the amplitude of the first peak of the first derivative of the fluorescence signal as discussed above with reference to FIGS. 5a–5d. Using methods discussed above with reference to FIG. 5, the oil and water holdups are coincidentally determined at 332, and using methods discussed above with reference to FIG. 5b (i.e., finding the amplitude of the second peak of the first derivative of the fluorescence signal), the water drop velocity is coincidentally determined at 334. Using the oil and water holdups and the water drop and oil velocities as determined, the water and oil volumetric flow rates are determined at 336.

As mentioned above, the tools according to the invention are advantageously used in conjunction with logging techniques wherein local holdup is measured at different locations in the well to determine where large quantities of water enter the well so that holes in the casing may be plugged.

There have been described and illustrated herein several embodiments of an optical probe for measuring three-phase characteristics of fluid flow at a single point in a hydrocarbon well and methods of processing signals generated by the probe. While particular embodiments of the invention have been described, it is not intended that the invention be limited thereto, as it is intended that the invention be as broad in scope as the art will allow and that the specification be read likewise. For example, while preferred fiber optic materials have been disclosed, fiber optics of other materials may be used provided that they have appropriate refractive indices to perform the functions described herein. In addition, while certain preferred angles have been disclosed with reference to the probe tip, other angles may be appropriate depending on the fiber optic material used. It will also be understood that various light sources and light detectors may be employed provided that they are capable of performing the functions described herein. For example, rather than using a laser diode source having a wavelength of 680–690 nm, a laser diode source having a wavelength of 470 nm could be utilized, or high intensity LEDs could be utilized in lieu of laser diodes. Further, while certain preferred calculation methods have been disclosed for determining holdup and volumetric flow rates from signals provided by optical probes, other calculation methods may be employed using the inventive probe system. It will therefore be appreciated by those skilled in the art that yet other modifications could be made to the provided invention without deviating from its spirit and scope as so claimed.

We claim:

1. An apparatus for analyzing a multiphase fluid flowing in a hydrocarbon well, comprising:

a) injection means for injecting a fluorescent tracer into the flowing fluid, said tracer selected from the group consisting of an oil soluble tracer and a water soluble tracer depending upon the continuous phase of the fluid;

b) a fiber optic probe having two ends, a first end being disposed in the flowing fluid a measured distance "d" downstream of said injection means;

c) a light source having a first wavelength such that said tracer will fluoresce at a second wavelength in response to illumination by said light source, said light source being optically coupled to a second end of said fiber optic probe;

d) light detection means optically coupled to said second end of said probe, said light detection means for detecting light at said second wavelength and for providing a first output signal indicative of detection; and e) processing means coupled to said injector means and said light detection means, said processing means including actuation means for causing said injection means to inject a volume of said tracer, and timing means for measuring the time between injection of said tracer and detection of said second wavelength by said light detection means.

2. An apparatus according to claim 1, wherein:
   the well has a diameter "D" and said measured distance "d" is between approximately 10D and approximately 100D.

3. An apparatus according to claim 2, wherein:
   the well has a diameter "D" and said measured distance "d" is equal to between approximately 22D and approximately 40D.

4. An apparatus according to claim 1, wherein:
   said processing means includes means for calculating velocity based on said distance "d" and said time between injection and detection.

5. An apparatus according to claim 4, wherein:
   said processing means includes means for determining an average velocity.

6. An apparatus according to claim 5, wherein:

said means for determining an average velocity includes means for determining when said first output signal peaks.

7. An apparatus according to claim 5, wherein:

said means for determining an average velocity includes means for determining maximum velocity and means for estimating average velocity based on maximum velocity.

8. An apparatus according to claim 1, wherein:

said light detection means detects light at said first wavelength and provides a second output signal indicative of detection at said first wavelength, and said processing means includes means for determining gas holdup based on said second output signal.

9. An apparatus according to claim 8, wherein:

said light detection means detects light at a third wavelength and provides a third output signal indicative of detection at said third wavelength, said third wavelength being a wavelength at which oil fluoresces when illuminated by light at said first wavelength, and said processing means includes means for determining oil holdup, oil velocity, or oil volumetric flow rate based on said third output signal.

10. A method of analyzing a multiphase fluid flowing in a hydrocarbon well, comprising:

a) injecting a fluorescent tracer in the fluid, the tracer being selected from the group consisting of a water soluble tracer and an oil soluble tracer depending upon the continuous phase of the fluid;

b) illuminating the fluid at a point downstream of the tracer injection, the point being a measured distance "d" from the tracer injection;

c) optically detecting fluorescing tracer at or near the point of illumination;

d) measuring the time between tracer injection and fluorescence detection.

11. A method according to claim 10, wherein:

said distance "d" is approximately between ten times and one hundred times the diameter of the well.

12. A method according to claim 10, further comprising:

calculating velocity of the continuous phase based on the time measured and the distance "d".

13. A method according to claim 10, wherein:

said step of detecting includes detecting a peak level of fluorescence, and said step of measuring the time includes measuring the time from injection to peak level detection.

14. A well production logging tool for analyzing a multiphase fluid flowing in a hydrocarbon well, comprising:

a) an elongate tool body having means for suspending said body in the well and means for diametrically locating said body in the well;

b) injection means coupled to a lower portion of said tool body for injecting a fluorescent tracer into the flowing fluid, said tracer selected from the group consisting of an oil soluble tracer and a water soluble tracer;

c) a fiber optic probe having two ends, a first end being coupled to an upper portion of said tool body a measured distance "d" downstream of said injection means;

d) a light source having a first wavelength such that said tracer will fluoresce at a second wavelength in response to illumination by said light source, said light source being optically coupled to a second end of said fiber optic probe;

e) light detection means optically coupled to said second end of said probe, said light detection means for detecting light at said second wavelength and for providing a first output signal indicative of detection; and f) processing means coupled to said injector means and said light detection means, said processing means including actuation means for causing said injection means to inject a volume of said tracer, and timing means for measuring the time between injection of said tracer and detection of said second wavelength by said light detection means.

15. A well logging tool according to claim 14, wherein:

the well has a diameter "D" and said measured distance "d" is between approximately 10D and approximately 100D.

16. A well logging tool according to claim 15, wherein:

the well has a diameter "D" and said measured distance "d" is equal to between approximately 22D and approximately 40D.

17. A well logging tool according to claim 1, wherein:

said processing means includes means for calculating velocity based on said distance "d" and said time between injection and detection.

18. A well logging tool according to claim 14, wherein:

said processing means includes means for determining an average velocity, said means for determining an average velocity including means for determining when said first output signal peaks.

19. A well logging tool according to claim 14, wherein:

said processing means includes means for determining an average velocity, and said means for determining an average velocity includes means for determining maximum velocity and means for estimating average velocity based on maximum velocity.

20. A well logging tool according to claim 14, wherein:

said light detection means detects light at said first wavelength and provides a second output signal indicative of detection at said first wavelength, said processing means includes means for determining gas holdup based on said second output signal, said light detection means detects light at a third wavelength and provides a third output signal indicative of detection at said third wavelength, said third wavelength being a wavelength at which oil fluoresces when illuminated by light at said first wavelength, and said processing means includes means for determining at least one of oil holdup, oil velocity, and oil volumetric flow rate based on said third output signal.

* * * * *